United States Patent [19]

Kita et al.

[11] 4,263,402

[45] Apr. 21, 1981

[54] PROCESS FOR PRODUCING 2,5-DIKETOGLUCONIC

[75] Inventors: Donald A. Kita, Essex, Conn.; Karlene E. Hall, Brooklyn, N.Y.

[73] Assignee: Pfizer Inc., New York, N.Y.

[21] Appl. No.: 79,668

[22] Filed: Sep. 28, 1979

[51] Int. Cl.³ .............................................. C12P 7/58
[52] U.S. Cl. ................................................... 435/137
[58] Field of Search ................................ 435/137, 138

[56] References Cited

U.S. PATENT DOCUMENTS

| | | | |
|---|---|---|---|
| 3,234,105 | 2/1966 | Motizuhn et al. | 435/138 |
| 3,790,444 | 2/1974 | Oga et al. | 435/137 |
| 3,998,697 | 12/1976 | Sonoyama et al. | 435/138 |

*Primary Examiner*—Alvin E. Tanenholtz
*Attorney, Agent, or Firm*—Francis X. Murphy; Charles J. Knuth; Peter C. Richardson

[57] ABSTRACT

A process for producing 2,5-diketogluconic acid which comprises aerobically propagating *Acetobacter cerinus* in a D-glucose-containing fermentation medium.

8 Claims, No Drawings

PROCESS FOR PRODUCING 2,5-DIKETOGLUCONIC

BACKGROUND OF THE INVENTION

This invention relates to the preparation of 2,5-diketogluconic acid.

Heretofore, 2,5-diketogluconic acid has been produced by several different varieties of bacteria such as *Acetobacter melanogenum, Acetobacter aurantium, Gluconoacetobacter rubiginosus, Gluconoacetobacter liquifaciens* and *Pseudomonas sesami*. The use of these microorganisms, however, is not satisfactory from an industrial point of view because of relatively low yields of 2,5-diketogluconic acid, relatively long fermentation times and because of the production of large amounts of brown or yellow-brown pigments as by-products of cultivation, thereby decreasing the purity of the desired 2,5-diketogluconic acid.

U.S. Pat. No. 3,790,444 relates to the production of 2,5-diketogluconic acid, without accompanying brown pigment, by a new species designated *Acetobacter fragum* ATCC No. 21409.

2,5-diketogluconic acid is useful as an intermediate for the preparation of ascorbic acid. A solution of 2,5-diketogluconic acid may be selectively reduced to 2-ketogulonic acid, which may be converted to ascorbic acid. The reduction of 2,5-diketogulonic acid may be effected by reduction with an alkali metal borohydride, as disclosed in U.S. Pat. No. 4,159,990, or by a fermentive reduction as described, for example, in U.S. Pat. Nos. 3,922,194, 3,959,076 and 3,963,574.

2,5-diketogluconic acid is also useful as an intermediate for the preparation of comenic acid by heating in the presence of an acid, as described, for example, in U.S. Pat. No. 3,654,316.

SUMMARY OF THE INVENTION

The present invention relates to the preparation of 2,5-diketogluconic acid by a process comprising aerobically propagating the microorganism *Acetobacter cerinus* in a glucose-containing fermentation medium. The glucose concentration in the fermentation medium is preferably between 10 and 15 percent (wt./vol.), most preferably between 11 and 13 percent. The propagation is preferably conducted at 25° C. to 30° C. and at a pH between 5 and 6. Particularly preferred microorganisms are *Acetobacter cerinus* strains IFO 3263 and IFO 3266. The 2,5-diketogluconic acid produced may be isolated from the fermentation medium or may be converted to 2-ketogulonic acid or to comenic acid.

DETAILED DESCRIPTION OF THE INVENTION 2,5-Diketogluconic acid is prepared in the process of the present invention in good yields without the formation of significant amounts of pigmented materials and in relatively short fermentation times. A number of strains of *Acetobacter cerinus*, including IFO 3262 (ATCC 12303), IFO 3263, IFO 3264, IFO 3265, IFO 3266, IFO 3267, IFO 3268 and IFO 3269 are publicly available and can be used in the present process for making 2,5-diketogluconic acid. Particularly preferred strains are IFO 3263 and IFO 3266.

Employing fermentation methods well known in the art, the *Acetobacter cerinus* is cultivated in a medium of which the main carbon source is D-glucose. It will be understood that, in accord with conventional fermentation practice, the fermentation medium will also contain sources of nitrogen, potassium, phosphorus and magnesium. The term "fermentation medium" in the specification and claims hereof is intended to define a medium containing such compounds. When employing the *Acetobacter cerinus* microorganisms in the present process, it is not necessary to use expensive organic nitrogen sources such as peptone or meat extract. The nitrogen can be economically provided by the use of urea or inorganic nitrogen sources, such as ammonium sulfate, ammonium nitrate, ammonium phosphate or similar salts, generally in amounts from between about 0.1 g. to 2 g./liter of fermentation medium, when nicotinic acid is also added as a growth factor, generally in an amount of about 0.2 to 10 mg./liter of fermentation medium. The potassium, magnesium and phosphorous are readily provided by the addition of salts such as potassium phosphate, ammonium phosphate, magnesium sulfate or similar salts, generally in amounts of about 0.1 to about 1 g./liter of fermentation medium. Considerable variation in the composition of the fermentation medium is, however, possible. Other suitable media will be readily apparent to those skilled in the art and the present process is not intended to be limited to the use of the particular media described above and in the Examples hereof. Glucose concentrations from about 2.5% to 20% (wt/vol) can be utilized in the present process. However, it has been found that initial glucose concentrations greater than about 15% cannot be tolerated by the microorganisms. Accordingly, total amounts of glucose greater than 15% (wt/vol) can only be utilized by conducting the fermentation at an initial glucose concentration of about 10% to 15% (wt/vol) and thereafter adding further increments of glucose to the fermentation medium during the course of the fermentation, the concentration of glucose in the medium not exceeding 15% (wt/vol) at any given time. Thus, the initial glucose concentration in the medium will normally range from about 2.5 to 15 percent (wt./vol.), preferably 10 to 15 percent, and most preferably between 11 and 13 percent, in order to obtain 2,5-diketogluconic acid most economically. The fermentation temperature is generally between about 20° and 35° C., preferably between 25° and 30° C., most preferably around 28° C. The initial pH of the culture medium may range from 3.5 to 7.5, and preferably from about 5 to 6. During the course of the fermentation the pH is desirably maintained in this range, preferably at about 5.5, for example by the addition of an alkali metal hydroxide, perferably sodium hydroxide solution. Alternatively, an alkali metal or alkaline earth metal carbonate, preferably calcium carbonate, may be used for pH control and is added for this purpose in medium makeup after autoclaving in an amount sufficient to give the desired pH, generally about 20 to 30 g./100 g. of glucose. It will be understood that the 2,5-diketogluconic acid will be produced in such fermentation media in the form of the corresponding alkali or alkaline earth metal salts, such as the sodium or calcium salts, and that such salts are embraced by the used of the term "2,5-diketogluconic acid" in the specification and claims hereof.

The *Acetobacter cerinus* microorganisms may also be employed to produce 2,5-diketogluconic acid in a fermentation medium containing from about 15 to 30 percent (wt./vol.) D-glucose and at least about 0.04 weight percent choline, based on the amount of glucose in the medium, as described in U.S. Patent Application Ser. No. 79,665 filed concurrently herewith.

After inoculation, the fermentation medium is agitated, for example with a mechanical stirrer at about 1700 r.p.m., and aerated at a rate of about 0.5 to 1 volume of air per volume of fermentation broth per minute. If desired, additional glucose can be added during the fermentation to replace some of the glucose utilized in the fermentation thereby increasing the overall yield of 2,5-diketogluconic acid.

The fermentation is continued until the desired yield is obtained. For example, employing *Acetobacter cerinus* IFO 3263 or 3266, a fermentation of about 35 to 40 hours will give a yield based on glucose, of about 90 to 95 percent of 2,5-diketogluconic acid. However, some variation in reaction times and yields are to be expected depending on the particular strain of microorganism, the glucose concentration in the fermentation medium and the cultivation temperature.

While not wishing to be bound by the following mechanism, it is believed that the conversion of glucose to 2,5-diketogluconic acid proceeds via the following pathways:

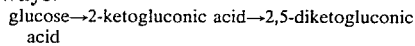
glucose→2-ketogluconic acid→2,5-diketogluconic acid

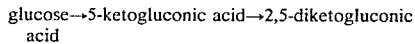
glucose→5-ketogluconic acid→2,5-diketogluconic acid

The intermediate 2-ketogluconic and 5-ketogluconic acids and 2,5-diketogluconic acid may be separated by paper chromatography using Whatman No. 1 and No. 4 paper and a solvent system of methyl ethyl ketone:acetone:formic acid:water (80:6:2:12). The acid spots are located by spraying with a 0.2 percent O-phenylenediamine ethanolic solution containing 1 percent nitric acid and heating to about 70° C. (5-ketogluconic acid-blue; 2-ketogluconic acid-yellow; 2,5-diketogluconic acid-green). High pressure liquid chromatography may also be used. Using the above methods, the progress of the fermentation can be followed.

2,5-diketogluconic acid may be separated and recovered from the final fermentation broth by any conventional procedures known to those skilled in the art. For example, the fermentation broth may be filtered, the pH of the aqueous filtrate adjusted to about 2 to 2.5 by the addition of a mineral acid such as hydrochloric acid, followed by concentration of the solution and addition of a lower alkyl alcohol, preferably ethanol or methanol. On standing, 2,5-diketogluconic acid in the form of its calcium or sodium salt separates from solution as a solid. The 2,5-diketogluconic acid may be obtained from the salt by treatment in dilute mineral acid, followed by, for example, treatment with a cation exchange resin, such as a sulfonic acid resin, for example, Dowex 50 (Dow Chemical Co.).

If desired, the fermentation broth may be processed to convert the formed 2,5-diketogluconic acid to other desired products, for example by fermentive reduction to 2-ketogulonic acid as described in U.S. Pat. Nos. 3,922,194, 3,959,076 or 3,963,574. Alternatively, the filtered fermentation broth may be used as a suitable reaction solution for the reduction of 2,5-diketogluconic acid to a 2-ketogulonic acid-containing solution by reaction with an alkali metal borohydride as described in U.S. Pat. No. 4,159,990. The 2-ketogulonic acid produced in these reactions is readily converted to ascorbic acid by means known in the art, for example by heating the methyl ester thereof in the presence of a base.

The present invention is illustrated by the following examples. However, it should be understood that the invention is not limited to the specific details of these examples.

EXAMPLE 1

The following aqueous inoculum medium was prepared:

| Ingredient | Grams/liter |
| --- | --- |
| Glucose | 25 |
| Corn steep liquor | 5 |
| $KH_2PO_4$ | 0.5 |
| $K_2HPO_4$ | 0.5 |
| $MgSO_4 . 7H_2O$ | 0.2 |
| $CaCO_3$ | 6.3 |
| | pH 6.2 |

A shake flask containing one liter of medium was autoclaved for 30 minutes at 121° C. Cells of *Acetobacter cerinus* IFO 3263 from a nutrient agar slant (5 ml of a 20 ml sterile aqueous suspension) were added to the flask which was then shaken on a rotary shaker at about 28° C. for about 24 hours. The pH of the cooled medium was 5.0.

An aliquot of the culture growth sufficient to provide a 5%, v/v inoculum was added to a 4-liter stirred fermentor containing 2 liters of the following production medium:

| Ingredient | Grams/liter |
| --- | --- |
| Glucose | 110 |
| Corn steep liquor | 0.5 |
| $(NH_4)_2HPO_4$ | 0.58 |
| $KH_2PO_4$ | 1.5 |
| $MgSO_4 . 7H_2O$ | 0.5 |
| Urea | 0.5 |
| $CuSO_4 . 5H_2O$ | 1 mg |
| Nicotinic acid | 0.3 mg |
| | pH 6.0 |

The fermentation was conducted at a temperature of about 28° C. with stirring at 1700 r.p.m. and aeration at the rate of 0.75 volume per volume of broth per minute. After a fermentation period of about 20 hours, sterile glucose was added (55 grams/liter). The pH was maintained at 5.5 by the addition of sodium hydroxide solution. The fermentation was continued until a yield of 2,5-diketogluconic acid of 95% (based on glucose) was obtained (36 hours).

EXAMPLE 2

Following the procedure of Example 1, *Acetobacter cerinus* strains IFO 3262, 3264, 3265, 3266, 3267, 3268 and 3269 were each tested. In each case, the fermentation product contained 2,5-diketogluconic acid in greater than 50% yield, together with some unconverted 2-ketogluconic acid and 5-ketogluconic acid intermediates. Higher yields of the desired 2,5-diketogluconic acid may be obtained by using longer fermentation times when employing these strains of *Acetobacter cerinus*.

We claim:

1. A process for producing 2,5-diketogluconic acid which comprises aerobically propagating *Acetobacter*

*cerinus* in a fermentation medium in which glucose is the main carbon source.

2. A process according to claim 1, wherein the initial glucose concentration of said medium is from 10 to 15 percent (wt./vol.).

3. A process according to claim 2 wherein the propagation is at a temperature between 25° to 30° C.

4. A process according to claim 2 wherein the pH of said medium is between about 5 and 6.

5. A process according to claim 1, wherein said *Acetobacter cerinus* is strain IFO 3263.

6. A process according to claim 1, wherein said *Acetobacter cerinus* is strain IFO 3266.

7. A process according to claim 5 or claim 6 wherein the glucose concentration is from 11 to 13 percent (wt./vol.) and said propagation is at a temperature between 25° C. and 30° C. and at a pH between 5 and 6.

8. A process according to claim 1 wherein said 2,5-diketogluconic acid is selectively reduced to 2-ketogulonic acid.

* * * * *